(12) United States Patent
Raab et al.

(10) Patent No.: US 6,794,543 B2
(45) Date of Patent: Sep. 21, 2004

(54) METHOD FOR PRODUCING ARYLPOLY (OXALKYL)-BENZYLDIMETHYL-AMMONIUM DERIVATIVES

(75) Inventors: Klaus Raab, Burgkirchen (DE); Gerhard Crass, Friedberg (DE); Rudolf Aigner, Kastl (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/276,210

(22) PCT Filed: May 3, 2001

(86) PCT No.: PCT/EP01/04963

§ 371 (c)(1),
(2), (4) Date: Nov. 14, 2002

(87) PCT Pub. No.: WO01/87818

PCT Pub. Date: Nov. 22, 2001

(65) Prior Publication Data

US 2003/0114533 A1 Jun. 19, 2003

(30) Foreign Application Priority Data

May 16, 2000 (DE) .......................... 10023955

(51) Int. Cl.$^7$ .......................... C07C 213/00
(52) U.S. Cl. ...................... 564/296; 514/643
(58) Field of Search .......................... 564/296; 514/643

(56) References Cited

U.S. PATENT DOCUMENTS

| | | | |
|---|---|---|---|
| 2,098,203 A | 11/1937 | Bruson | 250/150 |
| 2,115,250 A | 4/1938 | Bruson | 260/99.12 |
| 2,170,111 A | 8/1939 | Bruson | 260/293 |
| 3,875,215 A * | 4/1975 | Strycker | 260/501.15 |

FOREIGN PATENT DOCUMENTS

WO   WO 93/02040   2/1993

OTHER PUBLICATIONS

Database CAPLUS on STN, Acc. No. 1976:79595, GB 1283892 (abstract).*
Database CAPLUS on STN, Acc. No. 1966:75172, US 3236730 (abstract).*
Database CAPLUS on STN, Acc. No. 1963:448161, Bekhli et al., Meditsinskaya Promyshlennost SSSR (1962), 16(12), p. 7–11 (abstract).*

Houben–weyl, Methoden der Organischen Chemie, Georg Thieme Verlan Stuttgard, Band XI, (1958) pp. 592–599.
Journal of the American College of Toxicology, "Final Report on the Safety Assessment of Benzethonium Chloride and Methylbenzethonium" vol. 4, No. 5, 1985, Mary Ann Lieber, Inc., Publishers, pp. 65–106.
Stuart Warren, "Workbook for Organic Synthesis: The Disconnection Approach", John Wiley & Sons, 1982, pp. 49–51.

* cited by examiner

*Primary Examiner*—Brian Davis
(74) *Attorney, Agent, or Firm*—Richard P. Silverman

(57) ABSTRACT

The invention provides a process for preparing arylpoly (oxalkyl)benzyl-dimethylammonium derivatives of the formula (1)

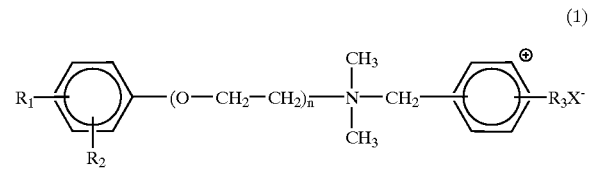

which comprises reacting compounds of the formulae (2) and (3)

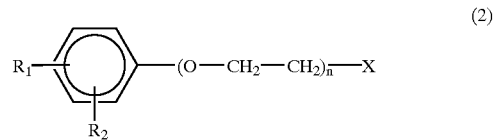

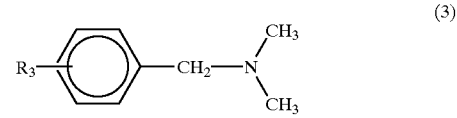

where
  X=Br, Cl, R—SO$_3$ with R=alkyl, alkylaryl
  R$_1$=H, C$_1$- to C$_{16}$-alkyl or O—C$_1$- to O—C$_{16}$-alkyl in the ortho, meta or para position,
  R$_2$=H, C$_1$- to C$_4$-alkyl or O—C$_1$- to O—C$_4$-alkyl,
  R$_3$=H, C$_1$- to C$_{16}$-alkyl or O—C$_1$- to O—C$_{16}$-alkyl in the ortho, meta or para position, and
  n=1, 2, 3 or 4,
at temperatures of from 60 to 160° C. in a solvent under the autogenous pressure.

13 Claims, No Drawings

METHOD FOR PRODUCING ARYLPOLY (OXALKYL)-BENZYLDIMETHYL-AMMONIUM DERIVATIVES

The present invention relates to a novel process for preparing arylpoly-(oxalkyl)benzyldimethylammonium derivatives by reaction of arylpoly-(oxalkyl) compounds with benzyldimethylamine or substituted benzyl-dimethylamines in a suitable solvent.

Some representatives of the compound class of arylpoly (oxalkyl)benzyl-dimethylammonium halides such as benzethonium chloride

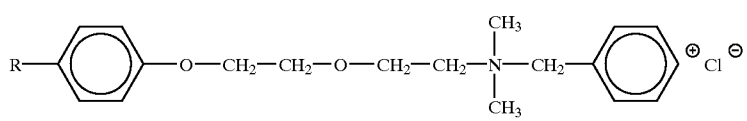

or methylbenzethonium chloride

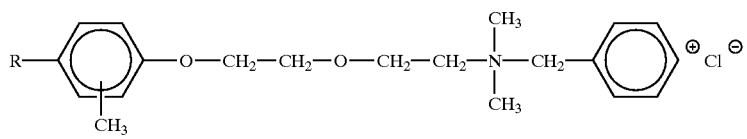

where $R=(CH_3)_3C-CH_2-C(CH_3)_2-$ have long been used commercially as biocides. These are crystalline powders whose purity requirements are described in various pharma-copeias. Solutions of these crystalline powders are also used. These compounds have bactericidal and fungicidal activity. Their areas of application as active components of formulations are, for example, disinfection in the hospitals sector, in the pharmaceutical sector or in the veterinary and foods sector. They are also used as preservatives for cosmetics such as hair conditioners, cleansing lotions or shampoos, in particular in rinse-off products, and also as odor control agents.

According to Workbook for Organic Synthesis: The Disconnection Approach, Stuart Warren, John Wiley & Sons, 1982, on pages 49 to 51 the preparation of such compounds where Y=H and R'=H according to the prior art is as shown in the equations 1 to 3.

Equation 1:

A

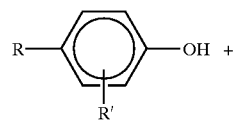

-continued

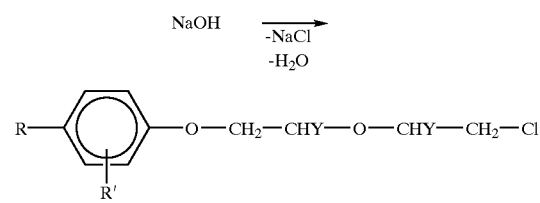

Equation 2:

B

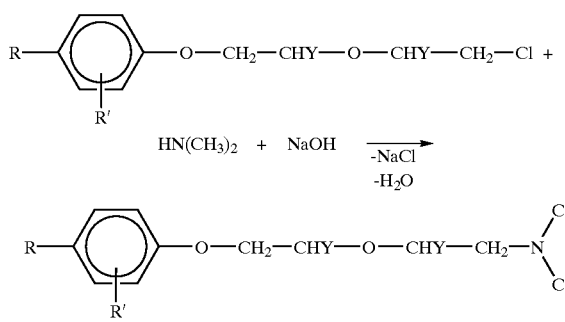

Equation 3:

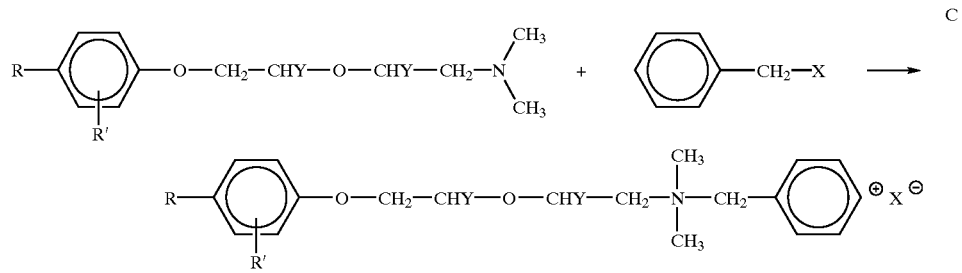

where

R is alkyl

R' is H, alkyl

Y is H, $CH_3$ or alkyl

X is Cl, Br.

U.S. Pat. No. 2,098,203 discloses arylpoly(oxalkyl) chlorides of the formula A where Y=H or $C_1$- to $C_5$-alkyl, R=$C_8$- to $C_{18}$-alkyl and R'=H, alkyl or alkoxy. Compounds of this type are the starting materials of the process of the invention.

U.S. Pat. No. 2,170,111 discloses tertiary amines of the formula B and further tertiary amines of similar structure to B. Their preparation takes place in a similar fashion to equation 2 by reaction of arylpoly(oxalkyl) chlorides of the formula A with amines such as dimethylamine, diethylamine, diethanolamine or morpholine, basic workup, washing and subsequent vacuum distillation.

Arylpoly(oxalkyl)benzyldimethylammonium chlorides of the formula C and also similarly substituted quaternary ammonium cations with further anions are disclosed in U.S. Pat. No. 2,115,250. They are obtained by reaction of the tertiary amines of the formula B or tertiary amines with a similar structure to B with alkylating agents such as benzyl chloride, dimethyl sulfate, diethyl sulfate, dimethyl oxalate, methyl iodide or ethyl bromide in a similar fashion to equation 3.

In Journal of the American College of Toxicology, Volume 4, Number 5, 1985 on page 66, the reaction of the required tertiary amines with benzyl chloride at 60 to 80° C. is likewise given as a route to benzethonium chloride and methylbenzethonium chloride.

In view of the complexity of this multistep reaction sequence including the necessary workup steps, and in view of the undesirable stoichiometric precipitation of sodium chloride or similar salts, it is an object of the present invention is to provide a simplified preparative process for arylpoly(oxalkyl)benzyldimethylammonium derivatives, in particular for benzethonium chloride or methylbenzethonium chloride.

This object is surprisingly achieved by a process involving the reaction of arylpoly(oxalkyl) compounds of the formula (2) with benzyldimethylamine or substituted benzyldimethylamines of the formula (3) in a suitable solvent to give the arylpoly(oxalkyl)benzyldimethylammonium derivatives of the formula (1).

The invention therefore provides a process for preparing arylpoly-(oxalkyl)benzyldimethylammonium derivatives of the formula (1)

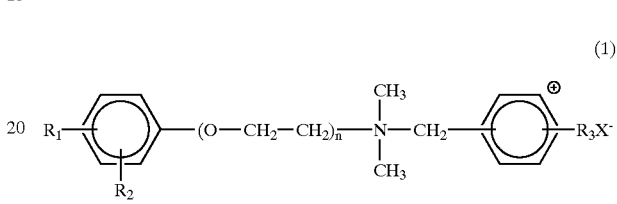

which comprises reacting compounds of the formulae (2) and (3)

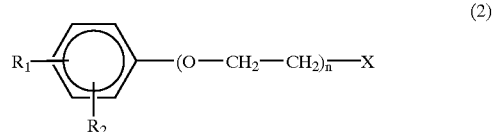

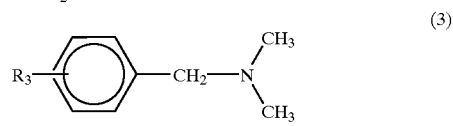

where

X=Br, Cl, R—$SO_3$ with R=alkyl, alkylaryl $R_1$=H, $C_1$- to $C_{16}$-alkyl or O—$C_1$- to O—$C_{16}$-alkyl in the ortho, meta or para position, $R_2$=H, $C_1$- to $C_4$-alkyl or O—$C_1$- to O—$C_4$-alkyl, $R_3$=H, $C_1$- to $C_{16}$-alkyl or O—$C_1$- to O—$C_{16}$-alkyl in the ortho, meta or para position, and n=1, 2, 3 or 4, at temperatures of from 60 to 160° C. in a solvent under the autogenous pressure in the closed reaction vessel.

$R_1$ is preferably $C_4$- to $C_{12}$-alkyl, in particular octyl or isooctyl in the para position. $R_2$ is preferably H or $CH_3$. n is preferably 2. $R_3$ is preferably H. X is preferably Cl.

When $R_1$=$(CH_3)_3C$—$CH_2$—$C(CH_3)_2$ in the para position, $R_2$=H, n=2, $R_3$=H, X=Cl, benzethonium chloride is obtained, and when $R_1$=$(CH_3)_3C$—$CH_2$—$C(CH_3)_2$ in the para position, $R_2$=$CH_3$, n=2, $R_3$=H, X=Cl, methylbenzethonium chloride is obtained. The processes for preparing these compounds constitute preferred embodiments of the invention.

Useful solvents for the process of the invention are preferably polar solvents, such as short-chain alcohols having from 1 to 6, preferably from 1 to 4 carbon atoms, which may be mono- or polyhydric, for example methanol, ethanol, isopropanol or monoethylene glycol, their mixtures with water and in particular water itself.

The arylpoly(oxalkyl) compounds of the formula (2) and the benzyldimethyl-amine or the substituted benzyldimethylamines of the formula (3) are preferably used in a molar ratio (2):(3)=1:0.95 to 1:1.05. The reaction is carried out at temperatures in the range from preferably 100 to 140° C., in particular from 115 to 130° C., under the autogenous pressure of the reaction mixture. The reaction times are preferably chosen so that the concentrations of the starting compounds of the formulae (2) and (3) determined by HPLC analysis of samples taken are as low as possible.

The arylpoly(oxalkyl)benzyldimethylammonium derivative of the formula (1) obtained from the reaction can be purified by recrystallization, for example from chloroform, ether, toluene or xylene. The solvent is preferably removed before recrystallization.

When water is used as the particularly preferred solvent in the reaction, the water can be removed for the purposes of workup after the end of the reaction, for example, by azeotropic distillation, vacuum drying, spray drying or fluidized-bed drying. The crude, water-free arylpoly(oxalkyl)-benzyldimethylammonium derivative of the formula (1) can be purified by recrystallization, for example from chloroform, ether, toluene or xylene.

The examples which follow illustrate the invention.

EXAMPLE 1

1 396 g of 2-(2-chloroethoxy)ethyl p-isooctylphenyl ether of the formula

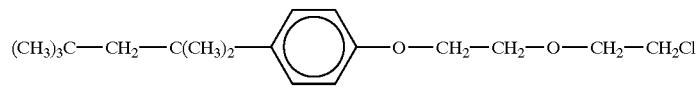

603 g of benzyldimethylamine and 1 000 g of demineralized water are stirred in a 5 liter autoclave under a nitrogen atmosphere for 20 hours at 120° C. and a pressure of 1.5 to 2.0 bar. The initially biphasic reaction mixture becomes monophasic in the course of the reaction. After depressurizing and cooling to about 80° C., the reaction mixture is transferred to a 10 liter stirred glass flask and admixed with 3 000 g of toluene. The water together with toluene is azeotropically distilled off with stirring. The colorless distillate separates into a toluene-containing upper phase, which is returned to the 10 liter stirred glass flask, and an aqueous lower phase, which is separated off. The yellow, clear water-free toluene solution is hot-filtered at about 110° C. through a heated pressure filter. The hot filtrate is slowly cooled to 30° C. under a nitrogen atmosphere and with slow stirring and addition of seed crystals. The resulting crystal slurry is filtered with suction and the crystals filtered off are washed repeatedly with toluene. The fine white crystals after they have been filtered off are dried at 80° C. under reduced pressure. The yield after drying is 70%. The product has a melting point of 162° C. and the purity determined by alkaline biphasic titration is above 99%.

EXAMPLE 2

443 g of 2-(2-chloroethoxy)ethyl p-isooctylphenyl ether of the formula

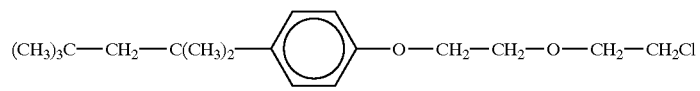

192 g of benzyldimethylamine and 320 g of distilled water are stirred in an autoclave under a nitrogen atmosphere for 15 hours at 120 to 125° C. and a pressure of 1.5 to 2.0 bar. The initially biphasic reaction mixture becomes monophasic in the course of the reaction. The autoclave is depressurized and the warm reaction mixture freed of water by feeding into a dryer at about 80° C. under reduced pressure. The now solid, water-free crude product is recrystallized from 950 g of toluene, washed repeatedly with toluene and dried at 80° C. under reduced pressure. The yield of fine white crystals is 72% and the purity determined by HPLC is $\geq 98\%$.

EXAMPLES 3 to 11

87.3 g of 2-(2-chloroethoxy)ethyl p-isooctylphenyl ether (a), 37.7 g of benzyldimethylamine and solvent (see table for quantity and type) are stirred in an autoclave under a nitrogen atmosphere at the autogenous pressure. The reaction conditions are listed in the table. Samples are taken of each crude product and analyzed by HPLC.

| Example | Quantity and solvent | Reaction temperature [° C.] | Reaction time [h] | Yield of unisolated product by HPLC [%] | Yield of (a) by HPLC [%] |
|---|---|---|---|---|---|
| 3 | 125 g water | 135 | 4 | 70 | 89 |
| 4 | 125 g water | 135 | 7 | 72 | 95 |
| 5 | 125 g water | 115 | 7 | 56 | 63 |
| 6 | 125 g water | 115 | 23 | 80 | 95 |
| 7 | 250 g water | 120 | 7 | 66 | 75 |
| 8 | 250 g water | 120 | 20 | 75 | 97 |
| 9 | 375 g water | 120 | 20 | 76 | 97 |
| 10 | 125 g methanol | 120 | 8 | 52 | 72 |
| 11 | 125 g monoethylene glycol | 120 | 8 | 65 | 86 |

The workup and purification take place in a similar fashion to example 2 by stripping off the solvent under reduced pressure, subsequent recrystallization from toluene or xylene and vacuum drying of the white crystals filtered off by suction.

What is claimed is:

1. A process for preparing an arylpoly(oxalkyl) benzyldimethylammonium derivatives of the formula (1)

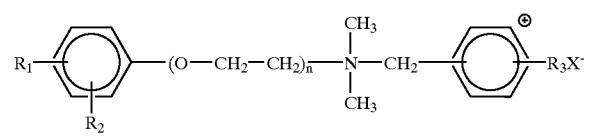

which comprises reacting compounds of the formulae (2) and (3)

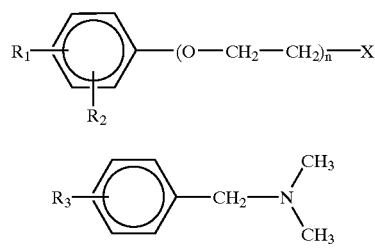

where

X=Br, Cl, R—SO$_3$ with R=alkyl, alkylaryl $R_1$=H, $C_1$- to $C_{16}$-alkyl or O—$C_1$- to O—$C_{16}$-alkyl in the ortho, meta or para position, $R_2$=H, $C_1$- to $C_4$-alkyl or O—$C_1$- to O—$C_4$-alkyl, $R_3$=H, $C_1$- to $C_{16}$-alkyl or O—$C_1$- to O—$C_{16}$-alkyl in the ortho, meta or para position, and n=2, 3 or 4, at temperatures of from 60 to 160° C. in a solvent under the autogenous pressure in the closed reaction vessel, wherein the reacting of compounds (2) and (3) is carried out in a polar solvent selected from the group consisting of short-chain alcohols having from 1 to 6 carbon atoms, water, and mixtures thereof.

2. The process as claimed in claim 1, wherein $R_1$ is $C_4$-to $C_{12}$-alkyl.

3. The process as claimed in claim 1, wherein $R_1$ is octyl or isooctyl in the para position.

4. The process as claimed in claim 1, wherein $R_2$ is H or $CH_3$.

5. The process as claimed in claim 1, wherein n is 2.

6. The process as claimed in claim 1, wherein $R_3$ is H and X is Cl.

7. The process as claimed in claim 1, wherein the reacting of compounds of formula (2) and the reacting of compounds of formula (3) are reacted in a molar ratio of from 1:0.95 to 1:1.05.

8. The process as claimed in claim 1, wherein the reacting of the compounds of formula (2) and the compounds of formula (3) comprises a temperature of from 100 to 140° C.

9. The process of claim 1, further comprising removing the polar solvent and purifying the arylpoly(oxalkyl) benzyldimethylammonium derivative of the formula (1) by recrystallization.

10. The process as claimed in claim 9, wherein the polar solvent comprises water and the polar solvent is removed in a removal step selected from the group consisting of azeotropic distillation using the toluene or xylene, vacuum drying, spray drying, fluidized-bed drying, and mixtures thereof.

11. The process as claimed in claim 1, wherein the reacting of compounds of formula (2) and the compounds of formula (3) comprises temperature of from 115 to 130° C.

12. The process of claim 1 wherein the arylpoly(oxalkyl) benzyldimethylammonium derivative of the formula (1) is selected from the group consisting of benzethonium chloride, and mixtures thereof.

13. A process for preparing benzethonium chloride or methylbenzethonium chloride comprising:

a) reacting compounds of the formulae (2) and (3)

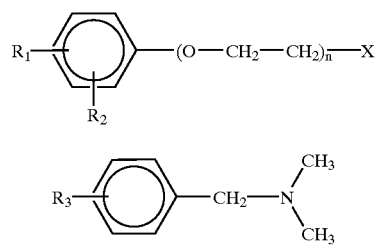

wherein

X=Cl $R_1$=isooctyl in para position, $R_2$=H or methyl, $R_3$=H, and n=2, at a temperature of from 100 to 140° C. in water under autogenous pressure in a closed reaction vessel;

b) removing the water, and c) recrystallizing the benzethonium chloride or methylbenzethonium chloride.

* * * * *